(12) United States Patent
Feinberg et al.

(10) Patent No.: US 7,887,829 B1
(45) Date of Patent: Feb. 15, 2011

(54) MUCOSAL CELL COMPOSITES AND METHODS

(75) Inventors: Stephen E. Feinberg, Ann Arbor, MI (US); Cynthia L. Marcelo, Ann Arbor, MI (US); Blake J. Roessler, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1369 days.

(21) Appl. No.: 10/281,940

(22) Filed: Oct. 28, 2002

Related U.S. Application Data

(60) Provisional application No. 60/341,505, filed on Oct. 26, 2001.

(51) Int. Cl.
*A61F 2/02* (2006.01)
(52) U.S. Cl. .................................... 424/422
(58) Field of Classification Search .............. 424/424, 424/425
See application file for complete search history.

(56) References Cited

U.S. PATENT DOCUMENTS 5,885,829 A  3/1999  Mooney et al.

OTHER PUBLICATIONS

Epidermis, Wikipedia.com, 2009.*
AAOMS, 1999; Evaluation of Ex Vivo Produced Oral Mucosa Grafts in SCID Mice; Izumi, p. 30.
AAOMS, 1999; Poster 46, Development of an Ex Vivo Produced Full Thickness Conjunctival Graft, Yoshizawa, p. 127.
J Oral Maxillofac Surg; 57:571-577, 1999; Ex-Vivo Development of a Composite Human Oral Mucosal Equivalent, Izumi, et al.
J. Dent Res 79(3): 798-805, 2000; Development and Characterization of a Tissue-engineered Human Oral Mucosa Equivalent Produced in a Serum-free Culture System, Izumi, et al.
AAOMS, 2001; Clinical Application of a Tissue-Engineered Ex Vivo-Produced Oral Mucosa Equivalent: A Preliminary Report; Izumi, et al., pp. 23-24.
AAOMS, 2001; A Tissue-Engineered Human Oral Mucosa: A New Approach Toward Clinical Application Xue, et al. p. 25.

* cited by examiner

*Primary Examiner*—Carlos A Azpuru
(74) *Attorney, Agent, or Firm*—Rader, Fishman & Grauer PLLC; James F. Kamp

(57) ABSTRACT

The present invention discloses a composite made of a layer of epithelial cells cultured together with a dermal matrix in a culture medium, which is free of BPE. The dermal matrix is a substantially non-immunogenic human dermis. Also disclosed is an enhanced composite where a biological agent has been introduced into the epithelial cells. The invention also comprises methods of making and implanting both the composite and the enhanced composite in an animal. A method of treating disease or injury through the use of the disclosed composites is also part of the present invention.

48 Claims, No Drawings

MUCOSAL CELL COMPOSITES AND METHODS

This application claims priority to U.S. Provisional Application Ser. No. 60/341,505, filed on Oct. 26, 2001.

This invention was made with government support under AR026009 and DE013417 awarded by the National Institutes of Health. The government has certain rights in the invention.

FIELD OF THE INVENTION

This invention relates to ex vivo produced mucosal cell composites ("composites"), methods of manufacturing composites and methods of using composites as research tools, reconstruction materials, biological agent delivery devices, and disease treatment devices.

BACKGROUND OF THE INVENTION

The epithelial membranes of the body, including the skin and the various mucosal membranes, have two layers. The surface layer or epithelial layer is mostly made of a type of epithelial cells called keratinocytes, while the underlying or dermis layer is a connective tissue which is fibrous and tightly attaches the keratinocytes to the sub-dermal layers.

An active area of research in the past several decades has been the development of human skin equivalents, which have a similar anatomical and biochemical make-up to whole skin, i.e., epidermis and dermis, and can be used to successfully treat trauma patients. The resulting skin equivalents can be applied to the trauma patients with relative ease.

A similar type of equivalent for the mucosal membranes of the body would be useful for reconstruction after trauma, surgical resection or preprosthetic surgery. The use of skin in procedures involving the mucosal membranes, however, presents several disadvantages, for example, a different pattern of keratinization between the keratinocytes of the skin and mucosal membranes. Thus, for this and other reasons, the techniques developed for skin equivalents are not readily transferable to the development of mucosal composites.

The development of mucosal equivalents has focused on the oral mucosa because of the ease of access and numerous procedures performed in the oral cavity. Previously, oral mucosa substitutes have involved split-thickness skin grafts or palatal or buccal oral mucosal grafts, both of which require at least a second surgical procedure. These procedures are unsatisfactory, though, because of the presence of adnexal skin structures, limited supply of mucosal grafts available and the uneven texture that results. Fabrication of cultured sheets of epithelial cells has been attempted in order to remedy these drawbacks. Known fabrication techniques, however, are also unsatisfactory because they rely on a feeder layer composed of irradiated mouse fibroblasts, thus risking introduction of murine DNA into proliferating human cells. The use of cultured sheets of epithelial cells has produced unsatisfactory results because they are fragile, difficult to handle, and tend to contract in size upon implantation. The addition of a dermal matrix of collagen gel has not improved fragility or ease of handling the cultured sheets of epithelial cells especially when used in the oral cavity which is laden with numerous collagenolytic enzymes. In addition, these cultured cells lack the rigidity necessary for easy transfer from the culture site to the site of use.

In addition, recent revelations that the new variant of Creutzfeldt-Jakob Disease (CJD) (colloquially "mad cow disease") is associated with meat and products which may utilize cattle brains has made it desirable to eliminate such products from all aspects of human medical treatments. This particularly pertinent in the cell culturing area because Fetal Bovine Serum (FBS) and Bovine Pituitary Extract (BPE) are common aspects of most protocols for the growth of cells. Indeed, the use of a defined culture medium, which eliminates the use of FBS and BPE from cell growth protocols, would be advantageous given the inherent unreliability of the contents of such FBS and BPE with respect to xenogeneic agents.

Moreover, the clinical usefulness of proteins and other therapeutic agents for the treatment of human disease is now well established. In addition to classic protein and peptide vaccines, these proteins may include, among others, cytokines, cytokine inhibitors or genetically engineered antibodies. Despite some clinical success, the systemic delivery of proteins continues to be problematic. Currently parenteral infusion or injection (intravenous, intra-muscular or subcutaneous) is the common route of administration. The short half-life of proteins requires frequent administration to consistently ensure the bioavailability of the injected proteins. The frequent administration also limits clinical usefulness of proteins.

The delivery of medicaments across the mucosal membranes is generally known. The delivery of proteins and other therapeutic agents transmucosally is an attractive alternative to known delivery routes for several reasons. Mucosal membranes have a high degree of vascularity. They are easily accessible for obtaining biopsies, re-transplantation and monitoring. The mucosal membranes are continually regenerated and their biology is well understood both at the cellular and molecular levels. Furthermore, the keratinocytes of the mucosal membranes are well suited for the delivery of gene products because these cells synthesize and export a wide variety of gene products to the extracellular space.

In order to have cells secrete a medicament, the medicament or medicament-producing agent must be introduced into the host cell or tissue. One method of introduction is known as transfection when a nucleic acid is introduced into the host cells or tissue. Various methods are known which introduce biological agents into host cells or otherwise transfect a host cell but generally fall into either viral or non-viral methods. Viral methods of introduction are less favored due to the inherently uncertainty that surrounds the safety of using viruses, especially with an eye toward the treatment of humans. The advantage of viral introduction methods is that the methodologies are well understood and highly effective at delivery of the introduced biological agent.

Thus, a need remains for compositions and method that enhance graft availability and suitability, while minimizing complication and risk, and that also enhance the testing, delivery and efficacy of therapeutic agents or methods.

SUMMARY OF THE INVENTION

The present invention addresses this need by disclosing a composite made of a layer of epithelial cells cultured together with a dermal matrix in a culture medium, which is free of BPE. The dermal matrix is a substantially non-immunogenic human dermis. Also disclosed is an enhanced composite where a biological agent has been introduced into the epithelial cells.

The invention also comprises methods of making and implanting both the composite and the enhanced composite in an animal. A method of treating disease or trauma through the use of the disclosed composites is also part of the present invention.

DETAILED DESCRIPTION

Index

Mucosal Cell Composites and Method of Making
　The epithelial layer
　The dermal matrix layer
　The composite
Enhanced Mucosal Cell Composites and Method of Making
　Biological agents
　Introduction of biological agents
　Biochemistry and secretion of biological agents
　Method of Implanting Composites
　Method of Using Enhanced Mucosal Cell Composites
Examples
　Creation of oral mucosal composites
　　Preparation of the oral mucosal cell samples
　　Cell culturing
　　Preparation of the dermal matrix
　　Preparation of the composite
　　Evaluation of oral mucosal composites
　Creation of conjunctiva composites
　　Cell culture of conjunctival keratinocytes and production of composites
　　Cell culture of oral keratinocytes and production of composites
　　Histologic and immunohistochemical staining
　　Keratinocyte cell culture of conjunctiva and oral mucosa
　　Histologic characteristics of conjunctival native tissue and in vitro composites.
　　Histologic characteristics of oral mucosa native tissue and in vitro composites
　　Immunohistochemical findings of conjunctival native tissue and in vitro composites
　　Immunohistochemical findings of oral mucosa native tissue and in vitro composites
　Implantation of composites into mice
　　Production of ex vivo produced oral mucosa composite
　　Transplantation of composites into SCID mice
　　Histology and immunohistochemistry
　　Evaluation of vascularity and statistical analysis
　　Histologic analysis of the graft
　　Microvessel density
　Implantation of composites in humans
　　Autologous human implantation
　　Examples of implantation in humans
　Retroviral transfection
　　Cells Lines
　　Viral Supernatant Generation
　　Transductions
　　Medium Scale Transductions
　　Cell Line Comparisons
　　Localization Molecule Comparisons
　　Discussion
　Creation of enhanced composites]
Mucosal Cell Composites and Method of Making Embodiments of the present invention in the form of the mucosal cell composites (herein "composites" or "equivalents") are constructs with anatomic and handling properties similar to native mucosa. These composites can be used, for example, to test the efficacy of a particular delivery method or in vitro toxicology of a chemical and/or product production levels of various biological agents, and secretion of those agents, as well as in vivo grafting procedures to reconstruct damaged tissue in humans or as a method of delivery of biological agents to human. The composites comprise an epithelial layer and a dermal matrix layer produced in an environment substantially free of serum, transformed irradiated feeder cells, or bovine pituitary extract in a defined culture medium.

The Epithelial Layer

The epithelial layer of the composites preferably utilizes oral mucosa cells, though one skilled in the art will recognize that other mucosal membranes, including without limitation, conjunctival, gastro-intestinal (esophageal, pharyngeal), urogenital (vaginal, bladder, urethral, cervical), nasal and anal mucosal membranes are also capable of serving as a basis for the composites.

The epithelial layer of the composites, comprised mainly of keratinocytes, may be obtained from any source, animal or human. Some useful sources of samples include samples of discarded tissue from routine human dentoalveolar surgical procedures or samples obtained from human patients according to approved protocols. While mucosa samples may be surgically obtained, a punch biopsy may be utilized because there are fewer traumas to the surrounding tissue.

After obtaining a sample of the desired tissue, the cells are prepared according to known techniques to remove any excess tissue, the underlying connective tissue, and any remaining basal cells, which might be attached to the resultant epithelial layer of cells. Incubation with trypsinizing solution followed by mechanical separation is a common method of removing the underlying connective tissue. The cells of the epithelial layer are cultured and subcultured according to known techniques except that a defined culture medium is utilized which does not include FBS or BPE. Embodiments of the defined culture medium are more fully discussed below.

The Dermal Matrix Layer

The second aspect of the composite comprises a suitable dermal matrix layer that underlies the epithelial layer. The dermal matrix provides rigidity to allow easy transference of the composite from the culture medium to the site of use and to allow proper cell differentiation and attachment to occur. A useful dermal matrix layer comprises an at least substantially acellular, nonimmunogenic cadaveric human dermis. Such a matrix would eliminate the matrix as a route of introduction of xenogeneic agents. The dermal matrix layer may have a polarity with one side adapted to allow the attachment and growth of epithelial cells, while the other side is porous and allows the ingrowth of fibroblasts, angiogenic cells, other cells and blood vessels, which help integrate the composite to the site of use. One such suitable dermal matrix layer is AlloDerm® (LifeCell Co., Woodlands, Tex.). The dermal matrix layer is prepared by cutting the material to size, followed by rehydration in culture plates.

The Composite

The composite may comprise merely the epithelial layer and the dermal matrix layer, which have been cultured together to form a unitary construct, which is an equivalent to the native mucosal membrane. The composite is constructed by seeding the epithelial cell, i.e., keratinocytes, onto the dermal matrix and culturing the two components together while submerged in a defined culture medium for a period of time.

In some embodiments, no collagen needs to be added to the dermal matrix, but the dermal matrix layer may be presoaked with a solution of type I or type IV collagen. If presoaking with collagen is desired, then defined culture medium should be added after presoaking to neutralize the presoaking solution.

In one embodiment, without limitation, after initially culturing the cells in a submerged state, the composite is transferred to a tissue culture flask, which allows the composite to continue to grow at the air/liquid interface. Culturing the composite at the air/liquid interface encourages stratification of the epithelial layer. An organotypic tissue culture flask may be used to facilitate the culturing of the composite at the air/liquid interface, however conventional culture flasks may be advantageous due to the ease of handling and reduced cost as compared to organotypic flasks. One useful method of culturing the composite is where the composite is cultured in the submerged state for about 4 days, and then cultured ("floated") at the aid/liquid interface for 7-14 days.

The immunohistologic structure of the composite may be evaluated using known methods of visualization including Ki-67 nuclear antigen and GLUT1 staining. Further evaluation may be undertaken by monitoring mitochondrial succinate dehydrogenase.

Enhanced Mucosal Cell Composites and Method of Making

The embodiments of the basic composite discussed above may be modified to produce an enhanced embodiment, which is capable of delivering a biological agent to target tissues or cells. Any known method of introducing a biological agent into a host cell or tissue may be used to create enhanced composites.

By way of one example only, the composite may be transfected with DNA to introduce foreign DNA into the epithelial cells. Transfection may be accomplished by a variety of means known in the art including, among others, calcium phosphate-DNA co-precipitation, DEAE-dextran-mediated transfection, polybrene-mediated transfection, electroporation (this is the application of short and intense electric impulses to permeabilize cell membranes, i.e. open up pores, to allow extracellular molecules to enter into the cells), microinjection, liposome fusion, lipofection, protoplast fusion, retroviral infection, biolistics, and dendrimers.

One useful method of modifying the epithelial cells in the composite is through the use of a retro viral infection. Retroviral infection introduces one or more biological agents into the host cell or tissue, e.g., the epithelial cells of the composite.

Biological Agents

Biological agent of the present invention may comprise compositions that possess a biological activity or property having structural (e.g., binding ability), regulatory, or biochemical functions. Biological activities may include activities associated With biological reactions or events in a host that allow the treating, detection, monitoring, or characterization of biological reactions or events.

Biological activities include, but are not limited to, therapeutic activities (e.g., the ability to improve biological health or prevent the continued degeneration associated with an undesired biological condition), targeting activities (e.g., the ability to bind or associate with a biological molecule or complex), monitoring activities (e.g., the ability to monitor the progress of a biological event or to monitor changes in a biological composition), imaging activities (e.g., the ability to observe or otherwise detect biological compositions or reactions), and signature identifying activities (e.g., the ability to recognize certain cellular compositions or conditions and produce a detectable response indicative of the presence of the composition or condition).

The agents of the present invention are not limited to these particular illustrative examples. Indeed any biological agent may be used, including compositions that deliver or destroy biological materials, or cosmetic agents. The biological agents may comprise, for example, nucleic acids, antibiotics, chemotherapeutic agents, proteins, and organic or inorganic molecules or compounds. Such agents may or may not further comprise common pharmaceutically acceptable compositions (e.g., adjuvants, excipients, or diluents).

In one embodiment, without limitation, biological agents include nucleic acids (e.g., DNA, RNA, antisense oligonucleotides). Where the agent is DNA, the present invention is not limited by the nature of the DNA. The DNA may comprise a DNA that includes a gene encoding a protein. Useful DNA comprises a gene encoding a protein that promotes wound healing and/or a protein that promotes tissue vascularization. The DNA may be encompassed in a plasmid.

The DNA may comprise gene encoding cellular mediators and growth factors, including angiogenic factors, nerve growth factors, cytokines like interleukins, vascular endothelium growth factor (VEGF), tumor necrosis factor alpha (TNF-α), basic fibroblast growth factor (bFGF), epidermal growth factor (EGF), platelet derived growth factor (PDGF), and transforming growth factors alpha and beta (TGF-α, and TGF-β]). The DNA may comprise a gene encoding a reporter protein such as luciferase (LUC), chlorafenicol acethyl transferase (CAT), or β-galactosidase (b-gal).

The biological agent may comprise one or more of the aforementioned proteins (native or recombinant), or other purified proteins or vaccinating agents (e.g., compositions that promote or enhance an immunologic response in a host).

Genes associated with some embodiments of the present invention may comprise a nucleic acid (e.g., DNA) sequence that comprises coding sequences necessary for the production of a polypeptide or precursor. The polypeptide can be encoded by a full length coding sequence or by any portion of the coding sequence so long as the desired activity or functional properties (e.g., enzymatic activity, ligand binding, signal transduction, etc.) of the full-length or fragment are retained.

The term "gene" may also encompass the coding region of a structural gene and the including sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' non-translated sequences. The sequences that are located 3' or downstream of the coding region and which are present on the mRNA are referred to as 3' non-translated sequences.

The term "gene" may also encompass both cDNA and genomic forms of a gene. A genomic form or clone of a gene contains the coding region interrupted with non-coding sequences termed "introns" or "intervening regions" or "intervening sequences." Introns are segments of a gene, which are transcribed into nuclear RNA (hnRNA); introns may contain regulatory elements such as enhancers.

Introns are removed or "spliced out" from the nuclear or primary transcript; introns, therefore are absent in the messenger RNA (mRNA) transcript. The mRNA functions during translation to specify the sequence or order of amino acids in a nascent polypeptide.

In addition to containing introns, genomic forms of a gene may also comprise sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "antisense" is used in reference to DNA or RNA sequences that are complementary to a specific DNA or RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into a host cell, this transcribed strand combines with natural mRNA produced by the host cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

Where "amino acid sequence" is recited herein to refer to an amino acid sequence of a naturally occurring protein molecule, "amino acid sequence" and like terms, such as "polypeptide" or "protein," are not meant to limit the amino acid sequence to the complete, native amino acid sequence associated with the recited protein molecule.

The term "transgene" as used herein refers to a foreign gene that is placed into an organism. The term "foreign gene" refers to any nucleic acid (e.g., gene sequence) that is introduced into the genome of an animal by experimental manipulations and may include gene sequences found in that animal so long as the introduced gene does not reside in the same location as does the naturally occurring gene.

As used herein, the term "recombinant DNA molecule" as used herein refers to a DNA molecule that is comprised of segments of DNA joined together by means of molecular biological techniques.

Biochemistry and Secretion of Biological Agents

Once inside the host cells or tissue, the biological agent has been either directly or indirectly delivered to the target. In some embodiments, without limitation, direct delivery of the agent means that the agent is secreted from the cell into the extracellular space, where it acts upon the target tissue or is taken up by the target tissue.

In some embodiments, without limitation, indirect delivery means that the biological agent is modified in the cell prior to being secreted. For example, the biological agent may be in an inactive form and is rendered active following the introduction of the dendrimer complex to host cells or tissues. The biological agent, upon exposure to light or a change in pH (e.g., due to exposure to a particular intracellular environment), may be altered to assume its active form. Alternately, the agent may be attached to a protective linker (e.g., photo-cleavable, enzyme-cleavable, pH-cleavable) to make it inactive and become active upon exposure to the appropriate activating agent, e.g., UV light, a cleavage enzyme, or a change in pH. Indirect delivery may also comprise the transcription of the nuclei acid to form a gene product, where the gene product is secreted to the extracellular space.

In other embodiments, the biological agent may not be secreted, but rather is retained within the cell where it may effect a change in the biological activities of host cell, either directly or through a series of signal transductions.

Method of Implanting Composites

Once constructed as described above, the composite of the invention (with or without enhancement) can be implanted in an animal or a human. As one example only, without limitation, the implantation may be a xenograft. This is particularly useful in the situation where the safety and efficacy of a particular composite is being ascertained. For example, a composite based on human mucosa cells may be implanted in mice. While not preferred, xenograft implantation may be animal-to-human. The implantation may also be an animal-to-animal or a human-to-human allograft, especially between immunologically similar individuals.

One type of implantation is autologous implantation because of the absence of any immunologic rejection between the host and the graft. Again, implantation in animals is useful for testing the safety and effectiveness of any particular composite.

In addition, the mucosal tissue, which serves as the basis of the epithelial layer of the composite, can be transplanted into other sites. For example, an oral composite may be implanted in the conjunctiva of the eye. The ability to cross-tissue implant or graft the composite eliminates many of the limitations associated with other mucosal tissues and/or substitutes; i.e. the oral mucosa is easily accessed for biopsy for the cells necessary for fabrication of the composite and is also abundant in comparison with conjunctival tissue.

Implantation of the composites can be done in a number of situations, including, without limitation, safety and efficacy testing, reconstruction of damaged tissue at the site of implantation, or delivery of a biological agent at the site of implantation, or for a combination of reasons. The need for reconstruction may arise because of trauma, disease, and/or malignancy.

The method of implantation should be carried out using medically accepted surgical techniques. Generally, the composite is placed at the desired site and held in place by sutures, staples or an adhesive. A bandage, surgical stent or other device or other tissue, as dictated by the implantation site, may cover the implanted composite.

Method of Using Enhanced Mucosal Cell Composites

The enhanced composites may be used to treat trauma or disease. For example, the enhanced composite can be placed at an injury site, delivering biological agents, including proteins, to the damaged or diseased tissue. This method of treating trauma and disease with the present invention allows bioavailability of selected agents, e.g. proteins, consistently over time. This consistency means that no lapse in treatment will occur, thus enhancing recovery. The treatment is discrete in that one procedure can be used to deliver agents for several days or weeks, thus eliminating multiple injections or operations. The use of enhance composites is versatile because the types of traumas and diseases that can be treated with this method is unlimited.

Examples

The following examples serve to illustrate certain embodiments and aspects of the present invention and are not to be construed as limiting the scope thereof. In the experimental disclosure which follows, the following abbreviations apply:

eq (equivalents); μ (micron); M (Molar); μM (micromolar); mM (millimolar); nM (nanomolar); N (Normal); mol (moles); mmol (millimoles); μmol (micromoles); nmol (nanomoles); g (grams); mg (milligrams); μg (micrograms); ng (nanograms); L (liters); ml (milliliters); μl (microliters); cm (centimeter); mm (millimeters); μm (micrometers); ° C. (degrees Centigrade); PBS (phosphate buffered saline); and RT (room temperature).

Creation of Oral Mucosal Composites

Preparation of the Oral Mucosal Cell Samples

For mouse trials, discarded human oral mucosa was obtained from routine dentoalveolar surgical procedures. For human trials using autologous implantation, a selected patient was anesthetized and a 5.0 mm punch biopsy of the hard palate or retromolar trigone or maxillary tuberosity was done. In either case, the tissue specimen was placed into a transport solution of approximately 30 mM hydroxyethylpiperazine-N'-2-ethanosulfonic acid [HEPES], 10 mM glucose, 3 mM KCl, 130 mM NaCl, 1.0 mM $Na_2HPO_4$, pH 7.4, supplemented with 150 IU/ml penicillin, 150 μg/ml streptomycin, and 7.5 μg/ml amphotericin B (Fungizone) (Sigma Chemical Co., St. Louis, Mo.) ("Solution A"). In the human trial, the donor site was treated by covering the biopsy area with a cyanoacrylate dressing, Dermabond® (Ethicon, Somerville, N.J.). Alternately, other phosphate buffer solutions could be used such Delbecco's Phosphate Buffered Saline without Ca++ or Mg++supplemented with glucose, gentamycin and amphotericin B (Fungizone)

Oral mucosal samples in Solution A were scraped clean to remove blood and trimmed of excess tissue. The remaining mucosal tissue was punctured several times and submerged in a 0.04% trypsin (Sigma Chemical Co., St. Louis, Mo.) solution prepared in Solution A. The mucosal tissue in the 0.04% trypsin solution was incubated overnight at room temperature to allow the separation of the epithelial layer from the underlying connective tissue at the submucosal-mucosal junction. The trypsin was inactivated the next day by adding soybean tissue inhibitor (Sigma Chemical Co., St. Louis, Mo.) or a 0.0125% solution of trypsin inhibitor. The epithelial layer was mechanically separated from the submucosal layer and the interface area scraped to dissociate the underlying basal cells.

Cell Culturing

The basic culture medium, MCDB 153, was purchased as under the tradename Epilife™ and supplemented with the EDGS™ supplement (Cascade Biologics, Inc. Portland, Oreg.). Epilife™ is a basal medium containing essential and non-essential amino acids, vitamins, other organic compounds, trace minerals, and inorganic salts. Epilife™ does not contain calcium chloride, antibiotics, anti-mycotics, hormones, growth factors, or proteins. Epilife™ is based on HEPES, is bicarbonate buffered and has a pH of 7.4 when equilibrated in an incubator with an atmosphere of 5% $CO_2$/95% air.

The supplement EDGS™ contains purified bovine serum albumin (BSA) and purified bovine transferrin. Both bovine products were obtained from North American animals, which have been certified free from infectious and contagious diseases. The isolation process for these bovine components also comprises steps that inactivate viruses. EDGS™ also contains hydrocortisone, recombinant human insulin-like growth factor type-1 (rhIGF-1), prostaglandin E2 (PGE2) and recombinant human epidermal growth factor (rhEGF). $CaCl_2$ is added to the medium to obtain a final concentration of 0.06 mM. Finally, 25 μg/ml gentamycin (Sigma Chemical Co., St. Louis, Mo.), is added. The resultant culture medium is referred to as "defined culture medium."

The cell suspension was filtered (250μ mesh PGC Scientific, Gaithersburg, Md.), counted with a hematocytometer, and plated at $7.0 \times 10^6$ cells in 5 ml in defined culture medium per T-25 flask (Laboratory Science Co, Corning, N.Y.). The plated cell cultures were incubated at 37° C. in 5% $CO_2$. Culture medium was changed one day after the initial plating of cells. The cultures were fed three times per week with the defined culture medium. When cells reached 70-80% confluence, after 7-14 days, they were subcultured at $7.0 \times 10^5$ cells per T-25 flask.

Preparation of the Dermal Matrix

AlloDerm® was cut into appropriate sized pieces. The AlloDerm® samples were rehydrated in PBS without $Ca^{++}$ and $Mg^{++}$ and placed into culture plates (Costar, Cambridge, Mass.). A control group utilized collagen where the AlloDerm® was pre-soaked with 5 μg type IV human recombinant collagen (Fibrogen, Inc., South San Francisco, Calif.)/100 μl PBS for one hour to enhance attachment of seeded oral mucosal cells. In addition, 1.0 ml of high calcium (1.8 mM) defined culture medium was added to each microwell, prior to seeding of oral mucosal cells, to neutralize the presoaking solution.

Preparation of the Composite

The cultured oral mucosal cells from the second or third passage of actively dividing cells were used to seed onto the prepared AlloDerm®. The cultured mucosal cells were harvested by first washing with Solution A followed by addition of a solution of trypsin-EDTA (0.03%/0.01%) (Sigma Chemical Co., St. Louis, Mo.) at 37° C. Trypsin activity will be inhibited with an equal volume of 0.03% soybean tissue inhibitor (Sigma Chemical Co., St. Louis, Mo.). Disaggregated cells were collected, counted, spun and resuspended. A cell concentration of $1.25 \times 10^5$ cells/100 μl was placed onto the basement side of the prepared AlloDerm® and allowed to remain undisturbed for 30 minutes. At that time, 1.0 ml of defined culture medium was gently added to the microwells without disturbing the cells. The mucosal cell-AlloDerm® composites were then be cultured for four days, submerged in the microwells of the culture plate. The composites were fed daily during this time period with defined culture medium.

After incubating the composites in a submerged environment for 4 days, they were transferred to sterile tissue culture plates and allowed to "float" on the liquid surface. The medium was changed every 2-3 days. Growing the composites in the tissue culture plates allows the composite to grow at an air/liquid interface. This unique and novel "floating" technique of growing cells at the air/liquid surface encourages stratification of the epithelial layer. It also confers the advantage of fabricating composites of any size or shape thus not being limited by the geometric and size configuration of the tissue cultureware and thus being more cost effective and efficient in production of the composites. Floating was done for 7-14 days prior to use.

Evaluation of Oral Mucosal Composites

Composites, produced with and without collagen, were removed from the cultures at 4, 11, and 18 days post seeding, i.e. prior to floating, 7 days post-floating and 14 days post-floating, respectively. These composites were evaluated histologically. Oral mucosal cells cultured in defined culture medium had normal morphology, were able to be subcultured serially and were highly proliferative after the second passage. The successful rate for primary cultivation was high (greater than 90%). The oral mucosa composites in the non-collagen type IV-coated group had a normal appearance at different time points. On the day 4 composite (D4C), the monolayer of the mucosal cells integrated with the underlying AlloDerm®. The day 11 composite (D11C) showed continuous stratified epithelium with characteristic 4 layers, and the day 18 composite (D18C) showed more fully differentiated and stratified epithelium. In contrast, those in the collagen type IV-coated group showed the mucosal cells peeling off from the AlloDerm® in most cases.

Human oral mucosa composites can be developed without the risk of introducing exogenous DNA and viruses in the subsequent grafting procedure using the Epilife™ define medium. Type IV collagen precoating does not enhance the binding of the mucosal cells on the AlloDerm® and should be excluded from the procedure because the basement membrane of the AlloDerm® contains type IV collagen and laminin. Instead of using costly, size-limited organotypic tissue culture flasks, floating the mucosa composites in ordinary cultureware is not only a far simpler, more cost-effective method, but also a good solution for fabrication of large constructs of different sizes and shapes.

Creation of Conjunctiva Composites

Cell Culture of Conjunctival Keratinocytes and Production of Composites

Conjunctiva tissue, obtained from patients having ocular surgery, varied in size, from 0.2 $cm^2$ to 0.5 $cm^2$. Tissue samples were placed in Solution A, described above. Conjunctival tissue samples were incubated with 0.04% trypsin (Sigma Chemical, St. Louis, Mo., USA) solution, prepared in Solution A, overnight at room temperature. The tissues were then separated above the basal layer and the interface area was mechanically scraped gently in an excess of a solution of 0.03% trypsin inhibitor (Sigma Chemical, St. Louis, Mo., USA) to dissociate the basal cells from the submucosal layer. The resulting cell suspension was centrifuged and plated at $7.0 \times 10^6$ cells in defined culture medium per T-25 flask (Laboratory Science Co, Corning, N.Y., USA) and incubated at 37° C. in 5% $CO_2$. After the primary keratinocyte cultures were expanded sufficiently, they were seeded at cell densities of $1.25 \times 10^5/cm^2$ pieces of AlloDerm® coated with type IV collagen (Life Technologies, Gaithersburg, Md.). The composites were cultured, submerged in defined culture medium, for 4 days, then raised to an air/liquid interface for 7 days and 14 days using the organotypic tissue culture flasks (Organogenesis Inc, Canton, Mass.). These are referred to as conjunctival D4C, D11C and D18C, respectively. The defined culture medium was used with a high concentration of calcium, 1.8 mmol/liter.

Cell Culture of Oral Keratinocytes and Production of Composites

A comparison set of composites based on discarded oral mucosa was also produced. These composites are referred to as oral mucosal D4C, D11C, D18C, respectively.

Histologic and Immunohistochemical Staining

Samples of conjunctiva and oral mucosa tissues, conjunctiva and oral mucosa composites were fixed in 10% formalin, embedded in paraffin, cut at 5 μm sections and stained with hematoxylin and eosin. Selected sections were stained immunohistochemically for Ki-67 nuclear antigen (Ki-67) and "HeptG2/Erythroid/Brain" type glucose transporter (GLUT1). Ki-67 is a cell proliferation marker, and its expression is seen throughout the cell cycle except in G0.

The sections were treated with 0.3% hydrogen peroxide in methanol and exposed to microwave pretreatment which consisted of placing the sections in a pressure cooker filled with 0.01M citrate buffer (pH 6.0) and heated with a microwave for 14 min. After the sections were rinsed with 0.01M PBS (pH 7.2) supplemented with 0.5% skim milk and 0.05% Triton-X 100 (Sigma Chemical, St. Louis, Mo., USA) ("T-PBS"), they were incubated with 5% skim milk in T-PBS for 1 hour to block nonspecific protein binding sites. Sections were incubated in primary antibodies at 4° C. overnight. The following primary antibodies were used: monoclonal antibody to Ki-67 (MIB-1) (1:100) (Immunotech, Marseille, France) and polyclonal antibody to rabbit GLUT1 (1:100) (Chemicon International, Temecula, Calif., USA). After the sections were rinsed with PBS, they were incubated in biotinylated horse anti-mouse IgG for Ki-67 and in biotinylated goat anti-rabbit IgG for GLUT1 at room temperature for 30 minutes. They were then rinsed and incubated in avidin-biotin peroxidase complex at room temperature for 30 minutes (Vector laboratories, Burlingame, Calif., USA). After rinsing, they were treated with 0.02% 3,3'-diaminobenzidine (DAB) in 0.05M Tris-HCl buffer (pH 7.6) containing 0.05% hydrogen peroxide to visualize the reaction products. The specificity of the immunoreactions was checked by replacement of primary antibodies with non-immune mouse IgG for Ki-67 and non-immune rabbit IgG for GLUT1. The sections were counterstained with hematoxylin.

Keratinocyte Cell Culture of Conjunctiva and Oral Mucosa

Native conjunctiva yielded about $5.5 \times 10^6$ cells/$cm^2$ and oral mucosa yielded about $7 \times 10^6$ cells/$cm^2$. Cells from both tissue types were grown and amplified in defined culture medium. Sufficient cells for primary seeding onto the AlloDerm® were grown in vitro within 2 to 3 weeks. Morphological features of the cultured conjunctival keratinocytes were polygonal cell profiles and small size.

Histologic Characteristics of Conjunctival Native Tissue and In Vitro Composites Normal native conjunctival epithelium demonstrated stratified squamous cells. Basal and mid-layer cells were cuboidal, while more superficial cells assumed flattened profiles. In the superficial layer, the flattened cells contained less conspicuous nuclei. Conjunctival D4C was comprised of 1 or 2 cell thick continuous layers of flat cells on the AlloDerm®. The epithelial cells of conjunctival D11C, which were cultured submerged for 4 days and raised to air/liquid interface for 7 days showed cell layers 1 to 3 cells thick. The squamous epithelium of conjunctival D18C, cultured submerged for 4 days and raised to air/liquid interface for 14 days, showed stratified cell layers up to 4 cells thick. The superficial layer of the stratified epithelium demonstrated inconspicuous nuclei as seen in the native tissue.

Histologic Characteristics of Oral Mucosa Native Tissue and In Vitro Composites

Native oral mucosal epithelium consisted of stratified squamous cells. Basal cells were small and polygonal, increased in size in the mid-layers of the epithelium, and demonstrated progressive flattening in the superficial layers. The superficial cells were flat, exhibited increase eosinophilia due to keratinization, and contained smaller and less conspicuous nuclei.

The epithelium of oral mucosal D4C showed continuous monolayers of keratinocytes. D11C showed the epithelium on the composite was 3 to 6 cells thick. By day 18, the squamous epithelium of the D18C was stratified up to 8 cells thick and demonstrated superficial keratinization.

Immunohistochemical Findings of Conjunctival Native Tissue and In Vitro Composites Immunoreactivity for Ki-67 nuclear antigen was present in all layers of native conjunctival epithelium. Focal epithelial cells of D4C showed nuclear immunoreactivity. Progressively increased numbers of immunoreactive epithelial nuclei were evident in D11C and D18C. The majority of native conjunctival epithelial cells were immunopositive for GLUT1. Immunoreactivity was more intense in many of the basal and suprabasal cells. Immunopositivity was also seen in flat endothelial cells of substantia propria blood vessels. Virtually all of the epithelial cells of conjunctival D4C, D11C, and D18C were immunopositive.

Immunohistochemical Findings of Oral Mucosa Native Tissue and In Vitro Composites Immunoreactivity for Ki-67 nuclear antigen was seen in the basal and suprabasal layers of native oral mucosal epithelium. Focal nuclei of cells in the basal layer of D4C were immunopositive. Oral mucosal D11C and D18C showed progressive increases in the number of immunopositive nuclei in the deeper layers of the epithelia. Native oral mucosa epithelium exhibited strong immunohistochemical staining for GLUT1. Immunoreactivity was limited to the deeper layers of the epithelium and was lacking in the superficial keratinized layer. All epithelial cells of D4C and D11C showed immunopositive GLUT1 reactivity. D18C mimicked native oral mucosa with strong basilar and mid-layer immunoreactivity with absence of immunoreactivity in superficial, keratinized epithelial cells.

These results indicate that conjunctival and oral mucosal D18C, grown ex vivo, without serum or a feeder layer, are similar to their respective native tissue. The epithelia of the composites demonstrate high proliferative and glycolytic states as indicated by the presence of both Ki-67 nuclear antigen and GLUT1 immunoreactivity, particularly within proliferating basal keratinocytes. Due to their similarity to native conjunctiva, oral mucosal composites may be useful for eyelid reconstruction.

Implantation of Composites into Mice

Production of Ex Vivo Produced Oral Mucosa Composite

Cultures of human oral mucosa keratinocytes and ex vivo production of oral mucosa composites were generated in a serum-free culture system without the use of an irradiated xenogeneic feeder layer. Human oral keratinocytes were generated and amplified from trypsinized discarded human oral mucosa obtained from routine dentoalveolar surgical procedures. AlloDerm® (LifeCell Inc, Branchburg, N.J.) was rehydrated in phosphate buffered saline (PBS) one hour prior to use. Harvested and expanded human oral keratinocytes, cultured in a 0.15 mM Ca++ defined culture medium, supplemented with hydrocortisone, insulin, EGF and BPE, were seeded at a density of $1.25 \times 10^5$ keratinocytes per square centimeter onto the rehydrated AlloDerm® coated with collagen type IV (Life Technologies, Gaithersburg, Md.). The keratinocyte-AlloDerm® composites were cultured submerged in a 1.8 mM Ca++ defined culture medium for four days (D4C) and then at an air/liquid interface for an additional seven (D11C) or fourteen days (D18C) to generate composites.

Transplantation of Composites into SCID Mice

Using institution approved protocols, composites were grafted into a dorsal subcutaneous pouch of 7-8 week old SCID mice, strain C.B-17/IcrTac-scidfDF (Taconic, Germantown, N.Y.). Mice were anesthetized using inhalation anesthesia, methoxyflurane (Metofane#+, Priman-Moore Inc.). The dorsal skin of mice was disinfected with 95% ethanol. A full-thickness curvilinear incision was made down to the panniculus carnosus to create a subcutaneous pouch approximately 1.5 to 2.0 cm² in size to accommodate the 1.0 cm² composites. Composites were transferred to a subcutaneous pouch and overlaid with a circular piece of gas sterilized biomedical grade silicone sheeting, 0.127 mm thick (Specialty Manufacturing, Inc., Saginaw, Mich.), which was used to prevent adherence of the epithelial layer of the composite to the overlying connective tissue of the subcutaneous pouch. The open reticular portion of the AlloDerm® of the composite was grafted face down towards the muscular fascia. AlloDerm®, without an epithelial layer, was used as a negative control. Experimental groups consisted of the day 4, 11 and 18 composites, i.e., D4C, D11C, and D18C, respectively. Mice were sacrificed at days 3, 10 and 21 post-grafting. Five AlloDerm® controls (no epithelial layer) and fifteen D4C mice were sacrificed at each of the post-grafting days 3, 10 and 21. Ten mice were sacrificed at 3, 10 and 21 days post-grafting for the D11C and D18C.

Histology and Immunohistochemistry

Retrieved composites were fixed with 10% formalin and embedded in paraffin for histologic examination. Specimens were cut into five micron sections and stained with hematoxylin and eosin. Immunostaining for keratin 10/13, a differentiation marker, was performed with an avidin-biotin-peroxidase complex (ABC) method.

For detection of mouse vascular endothelial cells, immunohistochemical staining for Triticum vulgaris (Wheat germ agglutinin; WGA) lectin binding was used to determine revascularization by counting the number of microvessels within the dermal component. Sections were first treated with 2% hydrogen peroxide in methanol for thirty minutes to inhibit endogenous peroxidase, followed by 10% bovine serum albumin (BSA) (Sigma St. Louis, Mo., USA) for one hour. The sections were then incubated with biotinylated-WGA antibody (Sigma St. Louis, Mo., USA), diluted 1:20 in 1% BSA, for one hour at 37° C. and washed in PBS, followed by ABC method (Vector Laboratories, Burlingame, Calif., USA) for ten minutes. A solution of peroxidase substrate 3,3'-diaminobenzidine tetrahydrochloride was used for visualization of the resulting complex. The specificity of the immunoreactants was assessed by replacement of biotinylated WGA with sugar or PBS.

Evaluation of Vascularity and Statistic Analysis

To evaluate revascularization in each sample WGA lectin immunohistochemistry was used to assist in quantifying the number of invading endothelial cells. Since single endothelial cells as well as some fibroblasts and macrophages were immunopositive for WGA, lumen encircled by immunopositive cells was used to identify microvessel density that is indicative of neoangiogenesis and revascularization of the AlloDerm®. In accordance with the protocol used by Weidner et al., the highest number of vessel lumens within any 200× field was represented as the vessel count of the sample. Comparisons between groups were evaluated by a Mann-Whitney U test. Values of $p<0.05$ were considered to be statistically significant.

Histologic Analysis of the Graft

AlloDerm® grafts without epithelium consisted of dense collagen fibrils and an undulating papillary surface. A continuous keratinocyte monolayer was formed in vitro in D4C. The epithelial layer began to stratify and showed evidence of parakeratinization in D11C. A continued increase in stratification and differentiation of the epithelium was seen in D18C. Keratin 10/13, a differentiation marker, was not expressed in D4C or D11C. In D18C it was only visible in the superficial layer.

In the control AlloDerm® graft, without an epithelial layer, at 3 days post-grafting in vivo, a few spindle-shaped cells, similar to fibroblasts and/or endothelial cells, were seen infiltrating into the portion of the AlloDerm® that was in direct contact with the underlying muscular layer. The cellular infiltration into the AlloDerm® gradually increased in number in day 10 and 21 post-grafting transplants, but was localized at the base. At post-grafting day 21 there was evidence of infiltrating cells present in the superficial or upper portion of the AlloDerm®, however, vascularization was scarcely seen at the base or lower portion.

The epithelial monolayer of grafted D4C began to stratify at post-grafting day 3. In contrast to the AlloDerm® control, the D4C showed an increase in the number of fibroblasts and endothelial cells infiltration throughout the underlying AlloDerm®. At post-grafting day 10 epithelial stratification and differentiation continued to increase in D4C and was comparable to what was seen in pre-grafted D18C. Infiltrating spindle-shaped fibroblasts and a rounder cell infiltration indicative of re-vascularization were evident within the lower or basal portion of the AlloDerm® in the D4C at 3 days post-grafting when compared to the AlloDerm® controls. At day 21 post-grafting, the epithelium of D4C continued to stratify. This was directly correlated with an increase in cell infiltration within the AlloDerm® over the day 10 post-grafting specimens which was indicative of an increase in re-vascularization within the AlloDerm®.

The epithelial layer of D11C, at post-grafting days 3 and 10, continued to stratify and differentiate. An increase in fibroblastic and endothelial cell infiltration was seen at the AlloDerm®-muscle interface. A marked increase in cellular infiltration and re-vascularization throughout the entire AlloDerm® was seen at day 10 post-grafting. The infiltration and revascularization was more pronounced than observed in D4C at similar time intervals post-grafting. At day 21 post-grafting the highly keratinized and stratified epithelial layer showed signs of degeneration. The breakdown in the epithelial layer in D11C coincided with a decrease in the cellular infiltration and vascularity within the AlloDerm® subjacent to the epithelium. Cellular infiltration was still evident, though, within the basal or lower portion of the AlloDerm® with evidence of luminous structures.

The D18C, at 3 days post-grafting, showed signs of marked keratinization of the epithelial layer. This correlated with a marked increase in fibroblastic and endothelial cell infiltration seen at the inferior and superior portions of the AlloDerm®. At day 10, post-grafting, D18C epithelium continued to breakdown. The cellular infiltration and re-vascularization of the entire AlloDerm® continued to show a marked increase at day 10 post-grafting. Arrangement of the collagen fibrils within the AlloDerm® appeared less eosinophilic and random in nature. These findings were greater than seen in D4C but the same as was seen in D11C at day 10 post-grafting. At day 21 post-grafting there were remnants of necrotic epithelium. Although the luminous structures, cellular infiltration and revascularization were noted within the AlloDerm® the histologic appearance of collagen bundles appeared to be tighter and denser.

Immunohistochemical detection of keratin 10/13 was used to determine the differentiated state of the epithelium after grafting in both the D4C and D11C groups. No evidence of keratin 10/13 was observed in D4C at post-grafting day 3. As epithelial layers continued to stratify, in situ, both composites, D4C and D11C, showed an increase in the expression of keratin 10/13 than seen at time of initial grafting. Expression of keratin 10/13 within the stratified epithelium in the D4C was more prominent than seen in D11C at day 10 post-grafting.

Microvessel Density

WGA lectin binding allowed identification and counting of microvessels irrespective of the presence of red blood cells within the lumen. At day 3 post-grafting there was a significant increase ($p<0.05$) of the number of microvessels present in the AlloDerm® of the D18C over the other groups, D4C, D11C, and the AlloDerm® without epithelium. At 10 days post-grafting D4C, D11C and D18C were all significantly greater ($p<0.05$) than the AlloDerm® without epithelium, with both the D11C and D18C significantly greater ($p<0.05$) when compared to D4C. The D4C continued to increase at 21 days post-grafting with a precipitous drop in the number of microvessels present in both the D11C and D18C, which correlated, with degeneration of the epithelial layer.

As indicated, the presence of an intact and healthy epithelial layer significantly influenced secondary remodeling within the dermis of the composite by its synthesis and release of cytokines, enzymes and growth factors. Although the survival and thickness of overlying epithelium, in vivo, were dependent on the length of in vitro culturing of the composite at an air/liquid interface, the D11C contained the optimal balance of re-vascularity and epithelial activity. The advantage of using D11C for grafting is that it allows a shorter culture period to produce composites by 1 week over D18C without compromising on epithelial stratification or a decrease in fibrovascular ingrowth within the dermis. Advantage of D11C over D4C is the increased stratification of the epithelium resulting in enhanced vascularity of the underlying AlloDerm® after grafting is situ. Results may be improved upon the exclusion of type IV collagen and BPE from the protocol for making the composites.

Implantation of Composites in Humans

Autologous Human Implantation

The composite may be applied to patients who supplied the initial mucosal samples so that these will be autogenous grafts. The proposed procedures may be done either under intravenous sedation supplement with local anesthesia or under general anesthesia. The method of choice will be determined by extent of the surgery, medical status of the patient, and/or patient request or anxiety level.

For example, one type of implantation procedure is maxillofacial vestibuloplasty. The recipient donor site is prepared such that a supra-periosteal dissection will be made in the area to be grafted. The composite or free palatal mucosal graft is then applied to the supra-periosteal bed and secured in place with 4-0 vicryl, interrupted, sutures. A pre-fabricated surgical stent, previously made on a model of the patient's mandible, is then applied to the grafted area. The stent is then bordered trimmed with dental compound and lined with tissue conditioner to assure a tight and secure fit of the stent so that the graft, composite or free palatal mucosa, is maintained in place to minimize movement during the healing phase. Stents are secured to the mandible with three prolene circumandibular sutures. The surgical stents will remain in place for 2 weeks.

Another type of implantation procedure is a periodontal-free mucosa graft. All subjects meet the following inclusion criteria: 1) one facial mucogingival (MG) defect measuring 3.0 mm or lack of keratinized gingiva on a non-molar tooth, 2) radiographic evidence of sufficient interdental bone height (2 mm between crestal bone and CEJ), and 3) surgery to repair recession defect or increase width of keratinized gingival is clinically indicated or requested by the patient. Each participant receives initial therapy consisting of oral hygiene instruction, scaling and root planing, coronal polishing, and occlusal adjustment as needed prior to entry into the study. Recession sites are prepared according to the standard root coverage procedure. After achieving profound local anesthesia, the accessible root surface is planed smooth with a combination of hand instruments and burs to eliminate any surface contamination. The recipient site is prepared by performing two vertical partial thickness incisions from the cut gingival margin into the alveolar mucosa and connected with the sulcular incision horizontally into each adjacent papilla, at a level just coronal to the CEJ, to within 1 mm of the adjacent teeth. The incisions are extended to approximately twice the desired width of the attached gingival, allowing for contraction of the graft when healing is completed. The periosteum may be left covering the bone. The composite graft is then trimmed so that it covers the recipient sites adequately.

The composite graft is secured to the remaining gingiva or underlying periosteum with a chrome gut suture. Care is taken to ensure mucosal graft is firmly adapted to the recipient site and no dead space is existed. The periodontal pack is then applied to cover the graft for 1 week.

Upon removal of the surgical stent, at two weeks, or the periodontal pack at one week, grafts were clinically assessed for take (adequacy of healing), epithelial coverage, and graft contour and texture. One and six months after the grafting procedure a 5.0 mm biopsy is taken from the graft site for routine light microscopy.

Examples of Implantation in Humans

The study included 16 patients, 41 to 74 years old, diagnosed with epithelial dysplasia with squamous cell carcinoma of lateral portion of the tongue. Four weeks before surgery, a 5×5 mm$^2$ punch biopsy was taken of the hard palate. Oral keratinocytes were dissociated and expanded in a defined medium culture system in the absence of BPE and collagen as described above. Harvested keratinocytes were seeded onto AlloDerm® to fabricate a composite (cultured 4 days submerged and 7 days at the air/liquid interface), the composite was placed on the open wound and stabilized by a gauze bolster. Day 6 postoperatively, the bolster was removed and surface of the transplanted composite was scraped for cytologic examination. Patients were transnasally fed until postoperative day 8 and then placed on a soft diet. Grafted sites were evaluated by direct observation and photography. A punch biopsy was performed 4 weeks postoperatively.

AlloDerm® without epithelium and composites were successfully grafted in all cases. Gross appearance of grafted composite at postoperative day 6 showed a darker red color indicating an increase in vascularity. This was not seen in AlloDerm® without epithelial layer. The composites also showed less contraction and induration of the wound than grafted AlloDerm® without epithelial layer. Cytologic results showed the presence of small, round-shaped cells suggestive of the presence of basal cells on the composite but not the AlloDerm®. Histopathologic examination showed the surface of both the composite and the AlloDerm® were covered by a thick, regenerative epithelial layer at 4 weeks postgrafting. Vascular ingrowth composed of thin endothelial cells was seen in the underlying submucosal layer of the composites, whereas blood vessels lined with endothelial cells were present in AlloDerm®. Grafted composites and AlloDerm® both remodeled and formed a neodermis more rapidly than in in vivo animal studies. However, the more uniform reorganization of the dermis of the composite seems to indicate a more natural regenerative response with less inflammation within the neodermis.

Marked vascular in growth into the dermal component of the composite was consistent with less inflammatory reaction and granulation tissue formation than, seen with AlloDerm® alone, resulting in a more favorable wound healing response after intraoral grafting. The regenerative response noted in the composites, i.e. less inflammatory response and presence of a more mature dermis with enhanced vascularity, was indicative that the composite resulted in a quicker healing and acceptance of the grafted composite tissue after intraoral grafting than in the AlloDerm® alone.

Retroviral Transfection

This example optimized reaction conditions for the successful transduction of humanized Green Fluorescent Protein (huGFP) into an oral keratinocyte genome using a lentivirus vector system.

Cell Lines

293-T Cells (ATCC# CRL-11268) were transfected with 3 FLX vectors (described below) for FIV34FT10-huGFP production. Cells were maintained in Delbecco's modified eagle's media (DMEM) supplemented with 10% FBS at 37° C./5.0% $CO_2$.

Primary canine oral keratinocytes harvested from the buccal floor and cavity and were suspended. Cells were plated in a 6-well format and incubated overnight at 37° C./5.0% $CO_2$. Keratinocytes were maintained in EpiLife Medium with 10 mM calcium chloride and EpiLife Defined Growth Supplement (Cascade Biologicals). Subsequent to transduction, cells were grown at 32° C./5.0% CO2.

Viral Supernatant Generation

Promega's Profectin CaPO4 transfection kit was used to transfect 293-T Cells as per kit protocol. The FLX plasmids (Nolan Lab) p5CL-VSVG (envelope plasmid), pFLX-RSG (shuttle vector containing the RSV/huGFP expression cassette) and pCFWΔenv (vector containing replication genes) were used to generate FIV34FT10-huGFP FBS supplemented DMEM viral supernatant. Viral supernatant was harvested 72 hours post transfection. This viral supernatant represents a 1.0× stock. Half of the supernatant was concentrated 100× by spin centrifugation. Both concentrations of viral supernatant were distributed in 1 ml aliquots and stored at −80° C.

Transductions

Buccal cavity and floor oral keratinocytes were grown to ~60% confluence and transduced with 0.5×, 1.0×, and 100× FIV34FT10-huGFP viral supernatant in a 6-well micro-plate format. Cells were spin inoculated at 2500 rpm for 90 m to localize viral particles and host cells. Subsequent to spin inoculation, plates were placed at 32° C./5.0% CO2.

Several transductions were performed in the presence of virus-to-cell localization molecules to determine an optimal viral infectivity environment. 10 μg/ml and 20 Polybrene (Hexadimethrin bromide; Fisher) or 10 μg/ml and 20 μg/cm2 Retronectin (Takara) served as experimental localization molecule concentrations respectively.

Transduction efficiencies were determined by GFP expression. Keratinocytes expressing GFP fluoresce green under ultra-violet light; this was scored as a successful transduction/integration event. Ultra-violet imaging allowed for estimated transduction efficiencies and Fluorescent Activated Cell Sorting (FACS) analysis quantitated GFP expression.

Medium Scale Transductions

Medium-scale transductions were performed on buccal cavity keratinocytes to produce a large GFP expressing cell population. Oral keratinocytes were seeded in three E-well micro-plates coated with 20 μg/cm$^2$ Retronectin and 100× viral supernatant. Plates were placed at 32° C. to allow for cell adhesion and subsequent gene transfer and integration.

Cell Line Comparisons

Transduction efficiencies of oral keratinocytes harvested from the buccal cavity and floor were compared in the presence of Polybrene. GFP expression was qualified via ultra-violet florescence imaging. Buccal cavity keratinocytes demonstrated 10%-35% GFP expression across viral supernatant concentrations 96 hours post transduction; while buccal floor keratinocytes displayed reduced expression corresponding to increasing viral concentrations. This apparent inverse of GFP integration is difficult to interpret due to the high degree of relatedness between cell lines. However, the presence of specific cell membrane receptors or adhesion molecules may decrease initial viral entry into the cell. Also, the inherent toxicity of GFP and the VSV-G envelope may play a role in decreased integration frequencies.

Localization Molecule Comparisons

To determine the optimal localization molecule, buccal cavity keratinocytes were transduced in the presence of Polybrene or Retronectin. Both molecules serve to increase viral endocytosis by localizing virus and target cells. However, Polybrene accomplishes this by binding to and precipitating viral particles onto adherent cells, while Retronectin binds to VLA-4, -5 cell surface integrin receptors and virions.

At 1.0× supernatant concentrations, keratinocytes displayed vastly different infectivities. Transductions carried out in the presence of Polybrene produced ≦20% GFP expressing cells; while Retronectin produced fewer than 5%. However, 100× viral supernatant bound Retronectin displayed ≦45% GFP expressing cells; while Polybrene inoculations produced ≦30% GFP integration frequencies. Transduction reactions carried out in 10 μg localization molecule or no localization molecule displayed 8%-12% expression across supernatant concentrations Discussion Buccal cavity and floor keratinocytes were transduced with FIV34FT10-huGFP to produce recombinant GFP expressing cells for use in cell migration experiments. Several viral supernatant concentrations and localization molecules were tested to optimize infection conditions. Keratinocytes displayed the highest transduction efficiency when FIV34FT10-huGFP viral supernatant was concentrated 100× and allowed to bind to Retronectin coated plates previous to cell seeding. As cells become adherent, Retronectin bound virus is sandwiched between the adherent cell and localization molecule. Once more, this sandwiching effect does not allow the virus to be removed from the reaction after a defined incubation period, as is the case with Polybrene. Using this methodology, a medium scale transduction using $5.0 \times 10^6$ buccal keratinocytes, 100×FIV34FT10-huGFP supernatant, and Retronectin was performed.

Creation of Enhanced Composites

Enhanced composites were using the transfected canine keratinocytes utilizing the same procedure as described with respect to the making of oral mucosal cell composites. Briefly, the enhanced cells were cultured and used to seed onto the prepared AlloDerm®. The cultured, enhanced cells were harvested by first washing with Solution A followed by addition of a trypsin solution. Trypsin activity will be inhibited with a solution of soybean tissue inhibitor. Disaggregated cells were collected, counted, spun and resuspended. Cells were placed onto the basement side of the prepared AlloDerm® contained in microwells of a culture plate. Defined culture medium was used to submerge the cells in the microwells. The enhanced cell-AlloDerm® composites were then be cultured for four days, submerged in the microwells of the culture plate. The composites were fed daily during this time period with defined culture medium. After culturing, the composite may be used directly or frozen for later use. A comparison set of enhanced composites were made using a dermal matrix that is a substantially acellular, nonimmunogenic porcine dermis (XenoDerm® from LifeCell).

Both sets of enhanced composites were evaluated for production of GFP using confocal microscopy photography. In both sets, at day 1 and day 4 post culturing or thawing, photographs show persistent GFP within the keratinocytes on the surface of the composite. Of the two dermal matrices utilized, AlloDerm® provided more GFP at the surface of the composite than the XenoDerm®. These results show that enhanced composites continue to produce the gene product of the transfected nucleic acid even after culturing and/or the freeze thaw cycle.

Preferred embodiments of the present invention have been disclosed. A person of ordinary skill in the art would realize, however, that certain modifications would come within the teachings of this invention, and the following claims should be studied to determine the true scope and content of the invention. In addition, the methods and compositions of the present invention can be incorporated in the form of a variety of embodiments, only a few of which are described herein. It will be apparent to the artisan that other embodiments exist that does not depart from the spirit of the invention. While the invention has been specifically described in connection with certain specific embodiments thereof, it is to be understood that this is by way of illustration and not of limitation. Thus, the described embodiments are illustrative and should not be construed as restrictive.

We claim:

1. A mucosal membrane equivalent comprising:
an epithelial layer including epithelial cells; and
a dermal matrix layer,
wherein the epithelial layer and the dermal matrix layer form a composite and are substantially free of serum, transformed irradiated feeder cells, and bovine pituitary extract and wherein the epithelial cells are transduced or transfected to deliver a biological agent.

2. The mucosal membrane equivalent of claim 1, wherein the biological agent is a protein.

3. The mucosal membrane equivalent of claim 2, wherein the protein is a growth factor.

4. The mucosal membrane equivalent of claim 1, wherein the biological agent is a nucleic acid.

5. The mucosal membrane equivalent of claim 4, wherein the nucleic acid is DNA.

6. A method of making a mucosal membrane equivalent comprising:
culturing epithelial cells with a dermal matrix to form a unitary construct, wherein the culturing step includes culturing the epithelial cells and dermal matrix in a defined culture medium that is substantially free of serum, transformed irradiated feeder cells, and bovine pituitary extract.

7. A method of making a mucosal membrane equivalent comprising:
culturing epithelial cells with a dermal matrix in a defined culture medium that is substantially free of serum, transformed irradiated feeder cells, and bovine pituitary extract to form a unitary construct, wherein the culturing step includes culturing the epithelial cells and dermal matrix construct in a submerged state and culturing the epithelial cells and dermal matrix at an air/liquid interface after culturing in the submerged state.

8. A method of making a mucosal membrane equivalent comprising:
culturing epithelial cells with a dermal matrix in a defined culture medium that is substantially free of serum, transformed irradiated feeder cells, and bovine pituitary extract to form a unitary construct, wherein the culturing step includes seeding keratinocytes onto the dermal matrix and wherein the keratinocytes are conjunctival mucosal cells.

9. A method of making a mucosal membrane equivalent comprising:
culturing epithelial cells with a dermal matrix to form a unitary construct, wherein the culturing step includes:
presoaking the dermal matrix in a defined culture medium;
seeding keratinocytes onto the dermal matrix to form a unitary construct;
culturing the unitary construct in a submerged state in a defined culture medium that is substantially free of serum, transformed irradiated feeder cells, and bovine pituitary extract; and
culturing the unitary construct at an air/liquid interface.

10. The method of claim 9, wherein the culturing step includes presoaking the dermal matrix in a collagen solution before presoaking in the defined culture medium.

11. A method of making a mucosal membrane equivalent comprising:
culturing epithelial cells with a dermal matrix in a defined culture medium that is substantially free of serum, transformed irradiated feeder cells, and bovine pituitary extract to form a composite, wherein the culturing step includes transducing or transfecting the epithelial cells to deliver a biological agent.

12. The method of claim 11, wherein the biological agent is a protein.

13. The method of claim 12, wherein the protein is a growth factor.

14. The method of claim 11, wherein the enhancing step includes transfecting the epithelial cells with a nucleic acid.

15. The method of claim 14, wherein the transfecting step includes retroviral transfection.

16. The method of claim 14, wherein the culturing step includes:
presoaking the dermal matrix in a defined culture medium;
seeding transfected epithelial cells onto the dermal matrix to form a composite;
culturing the composite in a submerged state; and
culturing the composite at an air/liquid interface.

17. The method of claim 16, wherein the culturing step includes presoaking the dermal matrix in a collagen solution before presoaking in the defined culture medium.

18. The method of claim 17, wherein the defined culture medium lacks serum, feeder cells, bovine pituitary extract or combinations thereof.

19. A method of using a mucosal membrane equivalent comprising:
implanting a composite into a mammal, wherein the composite is comprised of an epithelial layer including epithelial cells and a dermal matrix layer that are substantially free of serum, transformed irradiated feeder cells, and bovine pituitary extract and wherein the epithelial cells are transduced or transfected to deliver a biological agent to the mammal.

20. The method of claim 19, wherein the biological agent is a nucleic acid.

21. The method of claim 19, further comprising the step of secreting a biological agent from the transduced or transfected epithelial cells.

22. The method of claim 21, wherein the secreted biological agent is a protein.

23. The method of claim 22, wherein the protein is a growth factor.

24. The method of claim 19, wherein the implanting step occurs in any mucosal tissue of the mammal.

25. A method of treating a mammal for disease or injury comprising:
implanting, at a disease or injury site, a composite into a mammal, wherein the composite is comprised of an epithelial layer including epithelial cells and a dermal matrix layer that are substantially free of serum, transformed irradiated feeder cells, and bovine pituitary extract and wherein the epithelial cells are transduced or transfected to deliver a biological agent to the mammal.

26. A method of treating a mammal for disease or injury comprising:
implanting, at a disease or injury site, a composite into a mammal, wherein the composite is comprised of an epithelial layer including epithelial cells and a dermal matrix layer that are substantially free of serum, transformed irradiated feeder cells, and bovine pituitary extract and wherein the epithelial cells are transduced or transfected to deliver a nucleic acid to the mammal.

27. A mucosal membrane equivalent comprising:
an epithelial layer including epithelial cells; and
a dermal matrix layer,
wherein the epithelial layer and the dermal matrix layer form a composite and
wherein the composite is substantially free of serum, transformed irradiated feeder cells, and bovine pituitary extract.

28. The mucosal membrane equivalent of claim 27, wherein the composite is formed in the absence of collagen.

29. The mucosal membrane equivalent of claim 27, wherein the dermal matrix is an at least substantially acellular and non-immunogenic matrix.

30. The mucosal membrane equivalent of claim 29, wherein the dermal matrix is a cadaveric human dermis.

31. The mucosal membrane equivalent of claim 30, wherein the epithelial cells are human epithelial cells.

32. The mucosal membrane equivalent of claim 30, wherein the dermal matrix has a first side adapted to allow attachment of epithelial cells and a second side adapted to allow ingrowth of cells and/or blood vessels.

33. The mucosal membrane equivalent of claim 32, wherein the cells are fibroblasts, angiogenic cells, or combinations thereof.

34. The mucosal membrane equivalent of claim 27, wherein the epithelial cells are human epithelial cells.

35. The mucosal membrane equivalent of claim 34, wherein the human epithelial cells are keratinocytes.

36. The mucosal membrane equivalent of claim 35, wherein the keratinocytes are oral mucosal cells.

37. The mucosal membrane equivalent of claim 35, wherein the keratinocytes are conjunctival mucosal cells.

38. The mucosal membrane equivalent of claim 35, wherein the composite is formed from culturing the epithelial layer with the dermal matrix.

39. A method of making a mucosal membrane equivalent comprising:
culturing epithelial cells with a dermal matrix in a defined culture medium that is substantially free of serum, transformed irradiated feeder cells, and bovine pituitary extract to form a composite.

40. The method of claim 39, wherein the culturing step includes presoaking the dermal matrix in a solution of collagen.

41. The method of claim 39, wherein the culturing step includes culturing the epithelial cells and dermal matrix composite in a submerged state.

42. A method of using a mucosal membrane equivalent comprising:
implanting a composite into a mammal, wherein the composite is comprised of an epithelial layer including epithelial cells and a dermal matrix layer that are substantially free of serum, transformed irradiated feeder cells, and bovine pituitary extract.

43. The method of claim 42, wherein the epithelial cells are keratinocytes.

44. The method of claim 42, wherein the composite is implanted into a human.

45. The method of claim 44, wherein the composite is implanted into oral mucosa.

46. The method of claim 44, wherein the composite is implanted into conjunctival mucosa.

47. The method of claim 6, wherein the unitary construct is formed in the absence of collagen.

48. A method of making a mucosal membrane equivalent comprising:
  culturing epithelial cells with a dermal matrix to form a composite, wherein the culturing step includes:
  presoaking the dermal matrix in a defined culture medium;
  seeding keratinocytes onto the dermal matrix to form a composite;
  culturing the composite in a submerged state in a defined culture medium that is substantially free of serum, transformed irradiated feeder cells, and bovine pituitary extract; and
  culturing the composite at an air/liquid interface.

* * * * *